United States Patent
Koripelly et al.

(10) Patent No.: US 9,522,921 B2
(45) Date of Patent: Dec. 20, 2016

(54) PHOTOCHROMIC SPIROOXAZINE COMPOUNDS

(71) Applicant: Sabic Global Technologies, B.V., Bergen Op Zoom (NL)

(72) Inventors: Girish Koripelly, Bangalore (IN); Mohamed Ashraf Moideen, Bangalore (IN); Pradeep Jeevaji Nadkarni, Bangalore (IN); Meghna Markanday, Bangalore (IN)

(73) Assignee: Sabic Global Technologies, B.V., Bergen Op Zoom (NL)

( * ) Notice: Subject to any disclaimer, the term of this patent is extended or adjusted under 35 U.S.C. 154(b) by 0 days.

(21) Appl. No.: 15/152,710

(22) Filed: May 12, 2016

(65) Prior Publication Data
US 2016/0297836 A1    Oct. 13, 2016

Related U.S. Application Data

(63) Continuation of application No. PCT/IB2016/051383, filed on Mar. 10, 2016.
(Continued)

(51) Int. Cl.
*G02B 5/23* (2006.01)
*C07D 498/10* (2006.01)
(Continued)

(52) U.S. Cl.
CPC ............... *C07D 498/10* (2013.01); *G02B 1/04* (2013.01)

(58) Field of Classification Search
USPC ............... 252/586; 359/241, 642; 427/145; 430/270.1, 345; 503/223
See application file for complete search history.

(56) References Cited

U.S. PATENT DOCUMENTS 5,066,818 A   11/1991   Gemert et al.
5,446,150 A    8/1995   Rickwood et al.
(Continued)

FOREIGN PATENT DOCUMENTS

EP    0141407 B1    6/1988
EP    0245020 B1    10/1991
(Continued)

OTHER PUBLICATIONS

Pierre Lareginie, Vladimir Lokshin, Andrb Samat, Robert Guglielmetti, and Gerard Pepe, First permanent opened forms in spiro [indoline-oxazine] series: synthesis and structural elucidation, J. Chem. SOC.P, erkin Trans. 2 107-111.*
(Continued)

*Primary Examiner* — Bijan Ahvazi
(74) *Attorney, Agent, or Firm* — Rodney B. Carroll; Conley Rose, P.C.

(57) ABSTRACT

A photochromic dye comprising at least one compound characterized by Formula I:

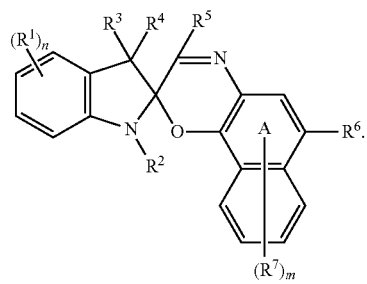

Formula I

22 Claims, 1 Drawing Sheet

Structure A in toluene after irradiation
Max Abs. @ 658 nm

Related U.S. Application Data

(60) Provisional application No. 62/146,826, filed on Apr. 13, 2015.

(51) Int. Cl.
*G02B 1/04* (2006.01)
*G03C 1/00* (2006.01)
*G03C 5/00* (2006.01)

(56) References Cited

U.S. PATENT DOCUMENTS

| | | | |
|---|---|---|---|
| 5,446,151 A | 8/1995 | Rickwood et al. | |
| 5,730,908 A | 3/1998 | Nodari et al. | |
| 6,114,437 A | 9/2000 | Brown et al. | |
| 6,303,673 B1 | 10/2001 | Clarke et al. | |
| 6,891,038 B2 | 5/2005 | Krongauz et al. | |
| 2005/0066453 A1 | 3/2005 | Chiu et al. | |

FOREIGN PATENT DOCUMENTS

| | | | | |
|---|---|---|---|---|
| EP | 0449669 A1 | 10/1991 | | |
| EP | 0524692 A1 | 1/1993 | | |
| EP | 0785936 B1 | 7/2002 | | |
| JP | 0439282 | * | 2/1992 | ............ C08K 5/15 |
| JP | H0472362 A | 3/1992 | | |
| JP | 3047434 B2 | 5/2000 | | |
| WO | 2010020770 A1 | 2/2010 | | |
| WO | 2012162725 A1 | 12/2012 | | |

OTHER PUBLICATIONS

Filing receipt and specification for provisional application entitled "Photochromic Spirooxazine Compounds," filed Apr. 13, 2016 as U.S. Appl. No. 62/146,826.

Filing receipt and specification for international application entitled "Photochromic Spirooxazine Compounds," filed Mar. 10, 2016 as application No. PCT/IB2016/051383.

Filing receipt and specification for GCC application entitled "Photochromic Spirooxazine Compounds," filed Apr. 12, 2016 as application No. 2016/31145.

Foreign communication from a related counterpart application International Application No. PCT/IB2016/051383, International Search Report and Written Opinion, May 18, 2016, 12 pages.

Perrier, Auriélie, et al., "Spectral Properties of Spirooxazine Photochromes: TD-DFT Insights," J. Phys. Chem. A, 2009, pp. 13004-13012, vol. 113, No. 46, American Chemical Society.

Maeda, Shuichi, "Spirooxazines," Chapter 2, Organic Photochromic and Thermochromic Compounds, 1999, pp. 85-109, vol. 1, Plenum Press, New York.

* cited by examiner

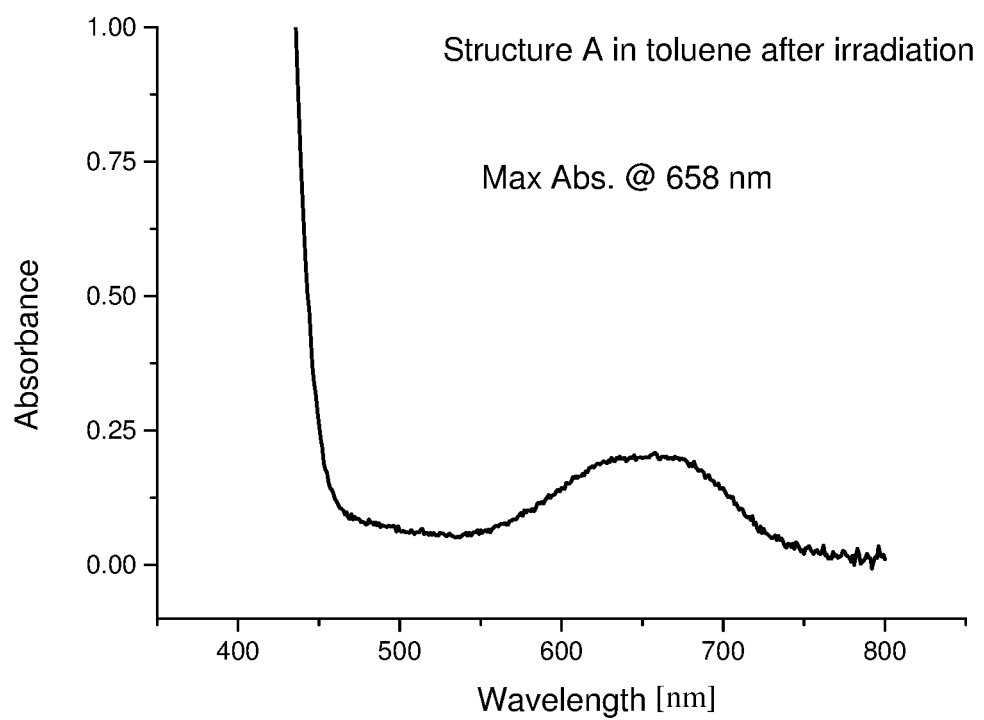

PHOTOCHROMIC SPIROOXAZINE COMPOUNDS

CROSS-REFERENCE TO RELATED APPLICATIONS

The present application is a continuation of and claims priority to International Application No. PCT/IB2016/051383 filed Mar. 10, 2016, entitled "Photochromic Spirooxazine Compounds," which claims priority to U.S. Provisional Application No. 62/146,826 filed on Apr. 13, 2015, entitled "Photochromic Spirooxazine Compounds," which applications are incorporated by reference herein in their entirety.

TECHNICAL FIELD

The present disclosure relates to photochromic dyes, more specifically to spirooxazine photochromic dyes.

BACKGROUND

Photochromic dyes are compounds that can reversibly change color, under the influence of environmental factors, such as for example light (e.g., ultraviolet light). Photochromic dyes are found in a variety of articles, most often lenses for glasses (e.g., photochromic lenses), automotive industry, sunroofs, etc. General classes of photochromic dyes include azobenzenes, salicylidene anilines, fulgides, spiropyrans, and spirooxazines. Very few photochromic dyes change color almost instantaneously when irradiated with light and also when an irradiation source is removed, while retaining the ability to repeatedly change color upon irradiation/removal of irradiation. Thus, there is an ongoing need to develop photochromic dyes.

BRIEF SUMMARY

Disclosed herein is a compound characterized by Formula I:

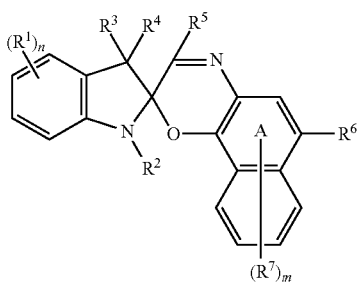

Formula I wherein $R^1$ and $R^7$ can each independently be (i) hydrogen or a group represented by formula —R, —OR, —SR, —COR, or —COOR, wherein R can be hydrogen, an alkyl group, an aryl group, or a heteroaryl group, (ii) a group represented by formula —Z, —CH$_2$Z, —CHZ$_2$, or —CZ$_3$, wherein Z can be a halogen, or (iii) —NO$_2$, —CN, or —SCN; wherein n is an integer from 1 to 4; wherein m is an integer from 1 to 5; wherein $R^2$ can be hydrogen, an alkyl group, a $C_1$ to $C_{20}$ alkyl group, an alkenyl group, a phenyl group, a mono-substituted phenyl group, a di-substituted phenyl group, a tri-substituted phenyl group, a phenylalkyl group, a benzyl group, a carbocyclic group, an alkylcarbocyclic group, a heterocyclic group, a heterocycloalkyl group, or an alkoxy group; wherein $R^3$ and $R^4$ can each independently be hydrogen, an alkyl group, an alkenyl group, a phenyl group, a mono-substituted phenyl group, a di-substituted phenyl group, a tri-substituted phenyl group, a phenylalkyl group, or a benzyl group, or wherein $R^3$ and $R^4$ are both part of the same alicyclic ring, wherein the alicyclic ring comprises a spirocarbon, wherein $R^3$ and $R^4$ are both linked to the spirocarbon, and wherein the alicyclic ring can be a cycloalkyl, norbornane, or adamantane; wherein $R^5$ can be hydrogen, an alkyl group, an alkoxy group, an aryl group, a heteroaryl group, or an amino group; and wherein $R^6$ can be an amino group represented by formula —NR'R", or an amino group comprising a heterocycloalkyl ring or a substituted heterocycloalkyl ring, wherein R' and R" can each independently be hydrogen, an alkyl group, a cycloalkyl group, an aryl group, a phenyl group, a mono-substituted phenyl group, a di-substituted phenyl group, a tri-substituted phenyl group, a naphthyl group, or a substituted naphthyl group.

Also disclosed herein is a photochromic dye composition comprising a photochromic dye and a polymeric material, wherein the photochromic dye can comprise at least one compound represented by Formula I:

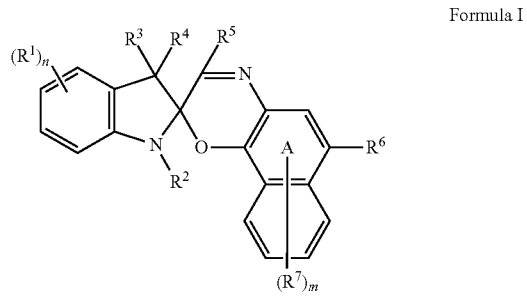

Formula I wherein $R^1$ and $R^7$ can each independently be (i) hydrogen or a group represented by formula —R, —OR, —SR, —COR, or —COOR, wherein R can be hydrogen, an alkyl group, an aryl group, or a heteroaryl group, (ii) a group represented by formula —Z, —CH$_2$Z, —CHZ$_2$, or —CZ$_3$, wherein Z can be a halogen, or (iii) —NO$_2$, —CN, or —SCN; wherein n is an integer from 1 to 4; wherein m is an integer from 1 to 5; wherein $R^2$ can be hydrogen, an alkyl group, a $C_1$ to $C_{20}$ alkyl group, an alkenyl group, a phenyl group, a mono-substituted phenyl group, a di-substituted phenyl group, a tri-substituted phenyl group, a phenylalkyl group, a benzyl group, a carbocyclic group, an alkylcarbocyclic group, a heterocyclic group, a heterocycloalkyl group, or an alkoxy group; wherein $R^3$ and $R^4$ can each independently be hydrogen, an alkyl group, an alkenyl group, a phenyl group, a mono-substituted phenyl group, a di-substituted phenyl group, a tri-substituted phenyl group, a phenylalkyl group, or a benzyl group, or wherein $R^3$ and $R^4$ are both part of the same alicyclic ring, wherein the alicyclic ring comprises a spirocarbon, wherein $R^3$ and $R^4$ are both linked to the spirocarbon, and wherein the alicyclic ring can be a cycloalkyl, norbornane, or adamantane; wherein $R^5$ can be hydrogen, an alkyl group, an alkoxy group, an aryl group, a heteroaryl group, or an amino group; and wherein $R^6$ can be an amino group represented by formula —NR'R", or an amino group comprising a heterocycloalkyl ring or a substituted heterocycloalkyl ring, wherein R' and R" can each independently be hydrogen, an alkyl group, a cycloalkyl group, an aryl group, a phenyl group, a mono-substituted phenyl group, a di-substituted phenyl group, a tri-substituted phenyl group, a naphthyl group, or a substituted naphthyl group.

Further disclosed herein is a photochromic dye comprising at least one compound characterized by Formula I:

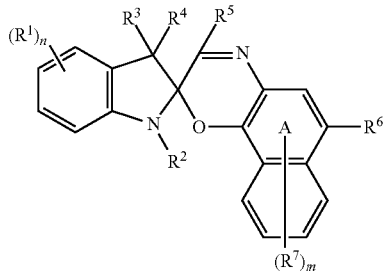

Formula I wherein $R^1$ and $R^7$ can each independently be (i) hydrogen or a group represented by formula —R, —OR, —SR, —COR, or —COOR, wherein R can be hydrogen, an alkyl group, an aryl group, or a heteroaryl group, (ii) a group represented by formula —Z, —$CH_2Z$, —$CHZ_2$, or —$CZ_3$, wherein Z can be a halogen, or (iii) —$NO_2$, —CN, or —SCN; wherein n is an integer from 1 to 4; wherein m is an integer from 1 to 5; wherein $R^2$ can be hydrogen, an alkyl group, a $C_1$ to $C_{20}$ alkyl group, an alkenyl group, a phenyl group, a mono-substituted phenyl group, a di-substituted phenyl group, a tri-substituted phenyl group, a phenylalkyl group, a benzyl group, a carbocyclic group, an alkylcarbocyclic group, a heterocyclic group, a heterocycloalkyl group, or an alkoxy group; wherein $R^3$ and $R^4$ can each independently be hydrogen, an alkyl group, an alkenyl group, a phenyl group, a mono-substituted phenyl group, a di-substituted phenyl group, a tri-substituted phenyl group, a phenylalkyl group, or a benzyl group, or wherein $R^3$ and $R^4$ are both part of the same alicyclic ring, wherein the alicyclic ring comprises a spirocarbon, wherein $R^3$ and $R^4$ are both linked to the spirocarbon, and wherein the alicyclic ring can be a cycloalkyl, norbornane, or adamantane; wherein $R^5$ can be hydrogen, an alkyl group, an alkoxy group, an aryl group, a heteroaryl group, or an amino group; and wherein $R^6$ can be an amino group represented by formula —NR'R", or an amino group comprising a heterocycloalkyl ring or a substituted heterocycloalkyl ring, wherein R' and R" can each independently be hydrogen, an alkyl group, a cycloalkyl group, an aryl group, a phenyl group, a mono-substituted phenyl group, a di-substituted phenyl group, a tri-substituted phenyl group, a naphthyl group, or a substituted naphthyl group.

BRIEF DESCRIPTION OF THE DRAWINGS

For a detailed description of the preferred embodiments of the disclosed compositions and methods of making and using same, reference will now be made to the accompanying drawing in which:

FIG. 1 displays an absorption spectrum in toluene of an open merocyanine form of a photochromic dye.

DETAILED DESCRIPTION

Disclosed herein are photochromic dye compositions and methods of using same. In an embodiment, a photochromic dye composition can comprise a photochromic dye and a polymeric material, wherein the photochromic dye can comprise at least one compound represented by Formula I:

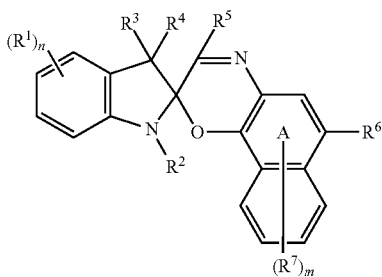

Formula I wherein $R^1$ and $R^7$ can each independently be (i) hydrogen or a group represented by formula —R, —OR, —SR, —COR, or —COOR, wherein R can be hydrogen, an alkyl group, an aryl group, or a heteroaryl group, (ii) a group represented by formula —Z, —$CH_2Z$, —$CHZ_2$, or —$CZ_3$, wherein Z can be a halogen, or (iii) —$NO_2$, —CN, or —SCN; wherein n can be an integer from 1 to 4; wherein m can be an integer from 1 to 5; wherein $R^2$ can be hydrogen, an alkyl group, a $C_1$ to $C_{20}$ alkyl group, an alkenyl group, a phenyl group, a mono-substituted phenyl group, a di-substituted phenyl group, a tri-substituted phenyl group, a phenylalkyl group, a benzyl group, a carbocyclic group, an alkylcarbocyclic group, a heterocyclic group, a heterocycloalkyl group, or an alkoxy group; wherein $R^3$ and $R^4$ can each independently be hydrogen, an alkyl group, an alkenyl group, a phenyl group, a mono-substituted phenyl group, a di-substituted phenyl group, a tri-substituted phenyl group, a phenylalkyl group, or a benzyl group, or wherein $R^3$ and $R^4$ can both be part of the same alicyclic ring, wherein the alicyclic ring can comprise a spirocarbon, wherein $R^3$ and $R^4$ can both be linked to the spirocarbon, and wherein the alicyclic ring can be a cycloalkyl, norbornane, or adamantane; wherein $R^5$ can be hydrogen, an alkyl group, an alkoxy group, an aryl group, a heteroaryl group, or an amino group; and wherein $R^6$ can be an amino group represented by formula —NR'R", or an amino group comprising a heterocycloalkyl ring or a substituted heterocycloalkyl ring, wherein R' and R" can each independently be hydrogen, an alkyl group, a cycloalkyl group, an aryl group, a phenyl group, a mono-substituted phenyl group, a di-substituted phenyl group, a tri-substituted phenyl group, a naphthyl group, or a substituted naphthyl group.

Other than in the operating examples or where otherwise indicated, all numbers or expressions referring to quantities of ingredients, reaction conditions, and the like, used in the specification and claims are to be understood as modified in all instances by the term "about." Various numerical ranges are disclosed herein. Because these ranges are continuous, they include every value between the minimum and maximum values. The endpoints of all ranges reciting the same characteristic or component are independently combinable and inclusive of the recited endpoint. Unless expressly indicated otherwise, the various numerical ranges specified in this application are approximations. The endpoints of all ranges directed to the same component or property are inclusive of the endpoint and independently combinable. The term "from more than 0 to an amount" means that the named component is present in some amount more than 0, and up to and including the higher named amount.

The terms "a," "an," and "the" do not denote a limitation of quantity, but rather denote the presence of at least one of the referenced item. As used herein the singular forms "a," "an," and "the" include plural referents.

As used herein, "combinations thereof" is inclusive of one or more of the recited elements, optionally together with a like element not recited, e.g., inclusive of a combination of one or more of the named components, optionally with one or more other components not specifically named that have essentially the same function. As used herein, the term "combination" is inclusive of blends, mixtures, alloys, reaction products, and the like.

Reference throughout the specification to "an embodiment," "another embodiment," "other embodiments," "some embodiments," and so forth, means that a particular element (e.g., feature, structure, property, and/or characteristic) described in connection with the embodiment is included in at least an embodiment described herein, and may or may not be present in other embodiments. In addition, it is to be understood that the described element(s) can be combined in any suitable manner in the various embodiments.

Unless defined otherwise, technical and scientific terms used herein have the same meaning as is commonly understood by one of skill in the art. The terms "polymer" and "polymeric material" as used herein include oligomers, homopolymers, and copolymers. The terms "polymer" and "polymeric material" can be used interchangeably for purposes of the disclosure herein.

Compounds are described herein using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, —CHO is attached through the carbon of the carbonyl group.

The term "alkyl" includes both $C_{1-30}$ branched and straight chain, alternatively $C_{1-20}$ branched and straight chain, saturated aliphatic hydrocarbon groups having the specified number of carbon atoms. Examples of alkyl include, but are not limited to, methyl, ethyl, n-propyl, i-propyl, n-butyl, s-butyl, t-butyl, n-pentyl, s-pentyl, n- and s-hexyl, n- and s-heptyl, n- and s-octyl, decyl, stearyl, and the like. For purposes of the disclosure herein, a $C_a$ to $C_b$ organic group (e.g., an alkyl group, a cycloalkyl group, an aryl group, etc.) includes groups represented by all integers between a and b, including a and b. For example, a $C_1$ to $C_{10}$ organic group includes $C_1$, $C_2$, $C_3$, $C_4$, $C_5$, $C_6$, $C_7$, $C_8$, $C_9$, and $C_{10}$ organic groups. Further, for example, a $C_6$ to $C_{12}$ organic group includes $C_6$, $C_7$, $C_8$, $C_9$, $C_{10}$, $C_{11}$ and $C_{12}$ organic groups.

The term "alicyclic" means a cyclic organic compound that is also aliphatic (e.g., comprises non-aromatic carbons). Alicyclic compounds can be monocyclic (e.g., cycloalkenes, cycloalkenes, etc.), bycyclic (e.g., norbornane, decalin, etc.), tricyclic (e.g., adamantane), or polycyclic (e.g., cubane).

The term "cycloalkyl" means a monovalent saturated aliphatic cyclic group, wherein all ring members are carbon (e.g., cyclopentyl, cyclohexyl, etc.)

The term "alkenyl" means a straight or branched chain, monovalent hydrocarbon group having at least one carbon-carbon double bond (e.g., unsaturated aliphatic hydrocarbon groups, ethenyl (—HC═CH$_2$)).

The term "alkoxy" means a straight or branched alkyl group (e.g., $C_{1-18}$) that is linked via an oxygen (i.e., alkyl-O—), for example methoxy, ethoxy, sec-butyloxy, and nonyloxy groups.

The term "alkylene" means a straight or branched chain, saturated, divalent aliphatic hydrocarbon group (e.g., methylene (—CH$_2$—), or propylene (—(CH$_2$)$_3$—)).

The term "cycloalkylene" means a divalent cyclic alkylene group, —$C_nH_{2n-x}$, wherein x represents the number of hydrogens replaced by cyclization(s). "Cycloalkenyl" means a monovalent group having one or more rings and one or more carbon-carbon double bond in the ring, wherein all ring members are carbon (e.g., cyclopentenyl, cyclohexenyl, etc.).

The term "aryl" means an aromatic hydrocarbon group (e.g., aromatic moiety) containing the specified number of carbon atoms (e.g., an unsaturated ring of six carbon atoms), which may optionally be substituted with one or more alkyl groups, and includes, for example phenyl, tolyl, xylyl, tropone, indanyl, indenyl, naphthyl, and the like.

The term "carbocyclic" means a cyclic group wherein all ring atoms are carbons, and it can be either saturated or unsaturated, such as for example cycloakyl, cycloalkylene, aryl, etc.

The term "alkylcarbocyclic" means a cyclic group wherein all ring atoms are saturated carbons, such as for example cycloalkyl.

The term "aryloxy" means an oxygen radical that is substituted with an unsaturated ring of six carbon atoms, which itself may optionally be substituted with one or more alkyl groups, and includes, for example, phenoxy.

The prefix "halo" means a group or compound including one more of a fluoro, chloro, bromo, iodo, and astatino substituent. A combination of different halo groups (e.g., bromo and fluoro) can be present. In an embodiment, only chloro groups are present.

The prefix "hetero" means that the compound or group includes at least one ring member that is a heteroatom (e.g., 1, 2, or 3 heteroatom(s)), wherein the heteroatom(s) can each independently be N, O, S, or P.

The term "heterocyclic" means a cyclic group wherein at least one ring member is a heteroatom, and it can be either saturated or unsaturated, such as for example heterocycloalkyl, heterocycloalkylene, heteroaryl, etc.

In an embodiment, a photochromic dye composition can comprise a photochromic dye and a polymeric material, wherein the photochromic dye can comprise at least one compound represented by Formula I:

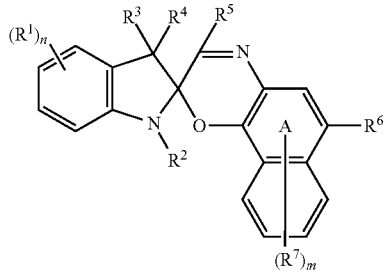

Formula I wherein $R^1$ and $R^7$ can each independently be (i) hydrogen or a group represented by formula —R, —OR, —SR, —COR, or —COOR, wherein R can be hydrogen, an alkyl group, an aryl group, or a heteroaryl group, (ii) a group represented by formula —Z, —CH$_2$Z, —CHZ$_2$, or —CZ$_3$, wherein Z can be a halogen, or (iii) —NO$_2$, —CN, or —SCN; wherein n can be an integer from 1 to 4; wherein m can be an integer from 1 to 5; wherein $R^2$ can be hydrogen, an alkyl group, a $C_1$ to $C_{20}$ alkyl group, an alkenyl group, a phenyl group, a mono-substituted phenyl group, a di-substituted phenyl group, a tri-substituted phenyl group, a phenylalkyl group, a benzyl group, a carbocyclic group, an alkylcarbocyclic group, a heterocyclic group, a heterocycloalkyl group, or an alkoxy group; wherein $R^3$ and $R^4$ can each independently be hydrogen, an alkyl group, an alkenyl group, a phenyl group, a mono-substituted phenyl group, a di-substituted phenyl group, a tri-substituted phenyl group, a phenylalkyl group, or a benzyl group, or wherein $R^3$ and $R^4$ can both be part of the same alicyclic ring, wherein the alicyclic ring can comprise a spirocarbon, wherein $R^3$ and $R^4$ can both be linked to the spirocarbon, and wherein the alicyclic ring can be a cycloalkyl, norbornane, or adamantane; wherein $R^5$ can be hydrogen, an alkyl group, an alkoxy group, an aryl group, a heteroaryl group, or an amino group; and wherein $R^6$ can be an amino group represented by formula —NR'R", or an amino group comprising a heterocycloalkyl ring or a substituted heterocycloalkyl ring, wherein R' and R" can each independently be hydrogen, an alkyl group, a cycloalkyl group, an aryl group, a phenyl group, a mono-substituted phenyl group, a di-substituted phenyl group, a tri-substituted phenyl group, a naphthyl group, or a substituted naphthyl group.

In some embodiments, $R^1$ can be hydrogen. In other embodiments, $R^1$ can be an alkyl group.

In an embodiment, $R^1$ can be selected from the group consisting of a methyl group, an ethyl group, a n-propyl group, an iso-propyl group, a n-butyl group, an iso-butyl group, a sec-butyl group, a tert-butyl group, a n-pentyl group, an iso-pentyl group, a sec-pentyl group, a hexyl group, a heptyl group, an octyl group, a nonyl group, a decyl group, a undecyl group, a dodecyl group, a tridecyl group, a tetradecyl group, a pentadecyl group, a hexadecyl group, a heptadecyl group, an octadecyl group, a nonadecyl group, and a dodecyl group.

In an embodiment, $R^1$ can be selected from the group consisting of hydrogen, a methyl group, an ethyl group, a n-propyl group, an iso-propyl group, a n-butyl group, an iso-butyl group, a sec-butyl group, and a tert-butyl group.

In an embodiment, $R^1$ can be a group represented by formula —R, —OR, —SR, —COR, or —COOR, wherein R can be hydrogen, an alkyl group, an aryl group, or a heteroaryl group. In such embodiment, R can be selected from the group consisting of a methyl group, an ethyl group, a n-propyl group, an iso-propyl group, a n-butyl group, an iso-butyl group, a sec-butyl group, a tert-butyl group, a n-pentyl group, an iso-pentyl group, a sec-pentyl group, a hexyl group, a heptyl group, an octyl group, a nonyl group, a decyl group, a undecyl group, a dodecyl group, a tridecyl group, a tetradecyl group, a pentadecyl group, a hexadecyl group, a heptadecyl group, an octadecyl group, a nonadecyl group, and a dodecyl group.

In an embodiment, $R^1$ can be a group represented by formula —Z, —CH$_2$Z, —CHZ$_2$, or —CZ$_3$, wherein Z can be a halogen. In such embodiment, Z can be F, Cl, Br, and the like, or combinations thereof.

In an embodiment, $R^1$ can be —NO$_2$, —CN, or —SCN.

In an embodiment, $R^2$ can be an alkyl group. In an embodiment, $R^2$ can be selected from the group consisting of a methyl group, an ethyl group, a n-propyl group, an iso-propyl group, a n-butyl group, an iso-butyl group, a sec-butyl group, a tert-butyl group, a n-pentyl group, an iso-pentyl group, a sec-pentyl group, a hexyl group, a heptyl group, an octyl group, a nonyl group, a decyl group, a undecyl group, a dodecyl group, a tridecyl group, a tetradecyl group, a pentadecyl group, a hexadecyl group, a heptadecyl group, an octadecyl group, a nonadecyl group, and a dodecyl group.

In an embodiment, $R^2$ can be selected from the group consisting of a methyl group, an ethyl group, a n-propyl group, an iso-propyl group, a n-butyl group, an iso-butyl group, a sec-butyl group, and a tert-butyl group. In an embodiment, $R^2$ is a methyl group.

In an embodiment, $R^3$ can be an alkyl group. In an embodiment, $R^3$ can be selected from the group consisting of a methyl group, an ethyl group, a n-propyl group, an iso-propyl group, a n-butyl group, an iso-butyl group, a sec-butyl group, a tert-butyl group, a n-pentyl group, an iso-pentyl group, a sec-pentyl group, a hexyl group, a heptyl group, an octyl group, a nonyl group, a decyl group, a undecyl group, a dodecyl group, a tridecyl group, a tetradecyl group, a pentadecyl group, a hexadecyl group, a heptadecyl group, an octadecyl group, a nonadecyl group, and a dodecyl group.

In an embodiment, $R^3$ can be selected from the group consisting of a methyl group, an ethyl group, a n-propyl group, an iso-propyl group, a n-butyl group, an iso-butyl group, a sec-butyl group, and a tert-butyl group. In an embodiment, $R^3$ is a methyl group.

In an embodiment, $R^4$ can be an alkyl group. In an embodiment, $R^4$ can be selected from the group consisting of a methyl group, an ethyl group, a n-propyl group, an iso-propyl group, a n-butyl group, an iso-butyl group, a sec-butyl group, a tert-butyl group, a n-pentyl group, an iso-pentyl group, a sec-pentyl group, a hexyl group, a heptyl group, an octyl group, a nonyl group, a decyl group, a undecyl group, a dodecyl group, a tridecyl group, a tetradecyl group, a pentadecyl group, a hexadecyl group, a heptadecyl group, an octadecyl group, a nonadecyl group, and a dodecyl group.

In an embodiment, $R^4$ can be selected from the group consisting of a methyl group, an ethyl group, a n-propyl group, an iso-propyl group, a n-butyl group, an iso-butyl group, a sec-butyl group, and a tert-butyl group. In an embodiment, $R^4$ is a methyl group.

In some embodiments, $R^5$ can be hydrogen. In other embodiments, $R^5$ can be an alkyl group.

In an embodiment, $R^5$ can be selected from the group consisting of a methyl group, an ethyl group, a n-propyl group, an iso-propyl group, a n-butyl group, an iso-butyl group, a sec-butyl group, a tert-butyl group. In an embodiment, $R^5$ is a methyl group.

In an embodiment, $R^6$ can be an amino group represented by formula —NR'R". In such embodiment, R' and R" can each independently be an aryl group, or alternatively a $C_6$ to $C_{10}$ aryl group. In an embodiment, R' and R" can each independently be selected from the group consisting of phenyl, 1-naphthyl, and 2-naphthyl.

In an embodiment, $R^6$ can be a N-phenyl-2-naphthyl amino group.

In some embodiments, $R^7$ can be hydrogen. In other embodiments, $R^7$ can be an alkyl group.

In an embodiment, $R^7$ can be selected from the group consisting of a methyl group, an ethyl group, a n-propyl group, an iso-propyl group, a n-butyl group, an iso-butyl group, a sec-butyl group, a tert-butyl group, a n-pentyl group, an iso-pentyl group, a sec-pentyl group, a hexyl group, a heptyl group, an octyl group, a nonyl group, a decyl group, a undecyl group, a dodecyl group, a tridecyl group, a tetradecyl group, a pentadecyl group, a hexadecyl group, a heptadecyl group, an octadecyl group, a nonadecyl group, and a dodecyl group.

In an embodiment, $R^7$ can be selected from the group consisting of hydrogen, a methyl group, an ethyl group, a n-propyl group, an iso-propyl group, a n-butyl group, an iso-butyl group, a sec-butyl group, and a tert-butyl group.

In an embodiment, $R^7$ can be a group represented by formula —R, —OR, —SR, —COR, or —COOR, wherein R can be hydrogen, an alkyl group, an aryl group, or a heteroaryl group. In such embodiment, R can be selected from the group consisting of a methyl group, an ethyl group, a n-propyl group, an iso-propyl group, a n-butyl group, an iso-butyl group, a sec-butyl group, a tert-butyl group, a n-pentyl group, an iso-pentyl group, a sec-pentyl group, a hexyl group, a heptyl group, an octyl group, a nonyl group, a decyl group, a undecyl group, a dodecyl group, a tridecyl group, a tetradecyl group, a pentadecyl group, a hexadecyl group, a heptadecyl group, an octadecyl group, a nonadecyl group, and a dodecyl group.

In an embodiment, $R^7$ can be a group represented by formula —Z, —$CH_2Z$, —$CHZ_2$, or —$CZ_3$, wherein Z can be a halogen. In such embodiment, Z can be F, Cl, Br, and the like, or combinations thereof.

In an embodiment, $R^7$ can be —$NO_2$, —CN, or —SCN.

In an embodiment of the compound characterized by Formula I, $R^1$ is hydrogen, $R^2$ is a methyl group, $R^3$ is a methyl group, $R^4$ is a methyl group, $R^5$ is hydrogen, $R^6$ is a N-phenyl-2-naphthyl amino group, and $R^7$ is hydrogen. In such embodiment, the compound characterized by Formula I can have Structure A:

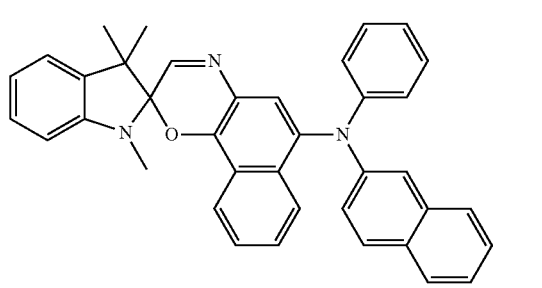

Structure A

In such embodiment, the compound characterized by Formula I comprises 1,3,3-trimethyl-N-(naphthalen-2-yl)-N-phenylspiro[indoline-2,2'-naphtho[1,2-b][1,4]oxazin]-6'-amine.

In an embodiment, the photochromic dye of this disclosure can be produced by using any suitable methodology. For example, the compound characterized by Formula I can be produced by reaction of a 1,2-naphthoquinone (1) (or a derivative thereof) with an amine (2) (e.g., N-phenyl-2-naphthyl amine), according to the following reaction scheme:

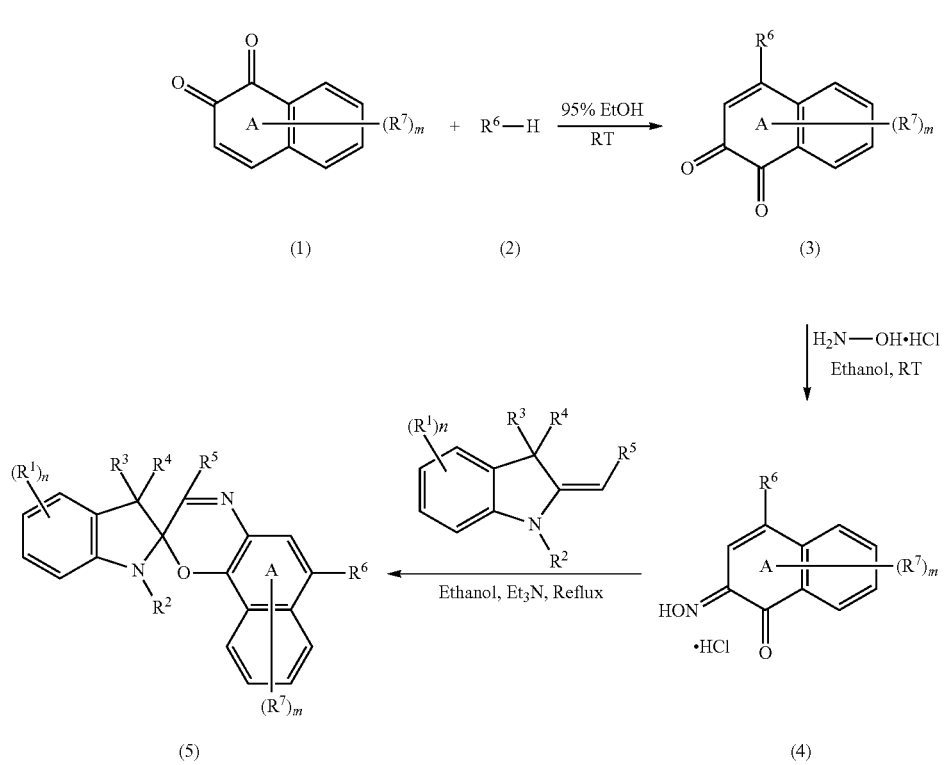

Nucleophilic addition of the amine (2) to the 1,2-naphthoquinone (1) (or a derivative thereof) with aqueous ethanol (95% EtOH) at room temperature (RT) followed by air oxidation can produce a compound (3) in almost quantitative yield. Oxime formation of 1,2-diketone with hydroxyl amine hydrochloride ($H_2N$—OH.HCl) can produce the desired mono-oxime derivative (4) in moderate yield. The final condensation step of the mono-oxime derivative (4) with an indoline or an indoline derivative (e.g., 1,3,3-trimethyleneindoline) in the presence of triethyl amine ($Et_3N$) under reflux conditions in ethanol can afford the desired spirooxazine compound characterized by Formula I.

In an embodiment, the compound characterized by Formula I can be a photochromic dye. Generally, photochromism is a well-known reversible phenomenon. A compound is said to be photochromic, when it changes color upon irradiation with ultraviolet (UV) light or radiation and returns back to its original color as the irradiation ceases. Generally, UV radiation can have a wavelength of from about 10 nm to about 400 nm. Commonly, the UV radiation from the Sun can be divided into three classes: UV-A (from about 315 nm to about 400 nm), UV-B (from about 280 nm to about 315 nm), and UV-C (from about 100 nm to about 280 nm). UV-C rays are almost completely absorbed by our atmosphere, and about 95% of UV-B rays are absorbed by ozone in the atmosphere. As will be appreciated by one of skill in the art, and with the help of this disclosure, for practical purposes, a photochromic dye will generally be irradiated with UV radiation in the UV-A range to undergo a reversible color change.

Generally, a dye is a compound that can impart a color to a substrate. Provided that the substrate is colorless, the dye gives the substrate its own color, and the intensity of the color generally depends on the amount of dye within the substrate. Further, a photochromic dye is a compound that can impart color to a substrate when irradiated with UV radiation. For example, a compound characterized by Formula I is a photochromic dye, and as such it can impart color to a polymeric material when irradiated with UV radiation. As will be appreciated by one of skill in the art, and with the help of this disclosure, a polymeric dye composition displays the color or appearance of the polymeric material (e.g., colorless) in the absence of the UV radiation.

In an embodiment, a photochromic dye of this disclosure can change color upon irradiation with UV-A radiation having a wavelength of from about 315 nm to about 400 nm, alternatively from about 325 nm to about 400 nm, or alternatively from about 340 nm to about 400 nm.

In some embodiments, the photochromic dye can be substantially colorless as perceived by a human eye while not irradiated with UV radiation. While irradiated with UV radiation, the photochromic dye can become colored as perceived by a human eye, e.g., the photochromic dye can absorb light (e.g., visible light) across the entire visible spectrum (e.g., from about 400 nm to about 750 nm, or alternatively from about 400 nm to about 700 nm). In an embodiment, the photochromic dye, upon UV-A irradiation, can absorb visible light and have a bluish-green color. In some embodiments, the photochromic dye, upon UV-A irradiation, can absorb visible light in a range of from about 540 nm to about 750 nm.

In an embodiment, the compound characterized by Formula I (e.g., closed form of compound characterized by Formula I) can undergo a ring opening upon irradiation with UV radiation ($hv_1$) to yield an open merocyanine form of the compound characterized by Formula I1, according to the following reaction scheme:

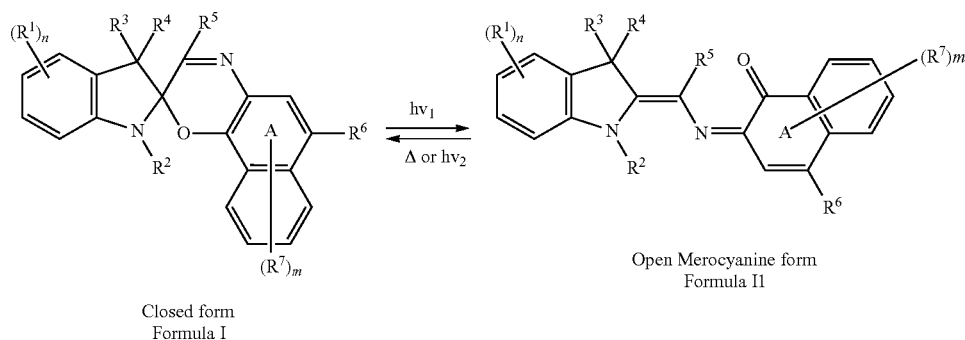

Closed form
Formula I

Open Merocyanine form
Formula I1

In an embodiment, the compound characterized by Structure A (e.g., closed form of compound characterized by Structure A) can undergo a ring opening upon irradiation with UV radiation ($hv_1$) to yield an open merocyanine form of the compound characterized by Structure A1, according to the following reaction scheme:

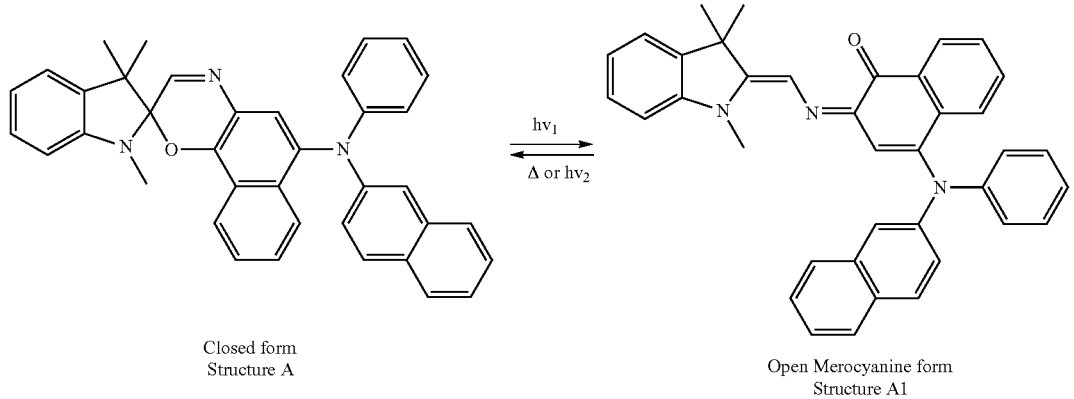 [SMILES: CN1c2ccccc2C(C)(C)C12C=Nc1cc(N(c3ccccc3)c3ccc4ccccc4c3)c3ccccc3c1O2 ; CN1/C(=C\N=C2\C=C(N(c3ccccc3)c3ccc4ccccc4c3)c3ccccc3C2=O)C(C)(C)c2ccccc21]

Closed form
Structure A

Open Merocyanine form
Structure A1

As will be appreciated by one of skill in the art, and with the help of this disclosure, the spiro form of an oxazine (e.g., closed form of compound characterized by Formula I, closed form of compound characterized by Structure A) is colorless, wherein the conjugated system of the oxazine and an aromatic part of the molecule are separated by a $sp^3$-hybridized "spiro" carbon. Further, as will be appreciated by one of skill in the art, and with the help of this disclosure, upon irradiation with UV radiation, a bond between the spiro carbon and the oxazine breaks, the ring opens, the spiro carbon achieves $sp^2$ hybridization and becomes planar, the aromatic group rotates, aligns its π-orbitals with the rest of the molecule, and a conjugated system forms having the ability to absorb photons of visible light, and therefore appears colorful. When the UV radiation source is removed ($hv_2$), the molecules characterized by an open merocyanine form gradually relax to their ground state, the carbon-oxygen bond reforms, the spiro carbon becomes $sp^3$ hybridized again, and the molecule returns to its colorless state characterized by a closed ring form.

In an embodiment, the photochromic dye of this disclosure (e.g., compound characterized by Formula I) can exhibit a bathochromic shift upon irradiation with UV radiation. Generally, the bathochromic shift (also referred to as a red shift) is a shift of a spectral band to lower frequencies (longer wavelengths) owing to the influence of substitution or a change in environment/structure. The photochromic dye of this disclosure can be substantially colorless when the irradiation (e.g., UV radiation) ceases.

In an embodiment, the photochromic dye of this disclosure (e.g., compound characterized by Formula I) can be characterized by a wide color range. As will be appreciated by one of skill in the art, and with the help of this disclosure, the substituents of the compound characterized by Formula I (e.g., $R^1$, $R^2$, $R^3$, $R^4$, $R^5$, $R^6$, $R^7$) can be varied, and as such the absorption spectrum of the open merocyanine form of the photochromic dye can vary, i.e., the color of the open merocyanine form of the photochromic dye can vary across the entire visible color spectrum.

In an embodiment, the photochromic dye of this disclosure (e.g., compound characterized by Formula I) can be characterized by a dye life of equal to or greater than about 500 coloration cycles, alternatively equal to or greater than about 1,000 coloration cycles, or alternatively equal to or greater than about 1,500 coloration cycles. Generally, the dye life refers to how many times a dye can change from a colorless state to a colored state and back to a colorless state (e.g., a coloration cycle) without substantially affecting the colorless state (which should remain substantially colorless) or the intensity of absorption that renders the color of the dye in the open merocyanine form.

In an embodiment, the photochromic dye of this disclosure (e.g., compound characterized by Formula I) can be soluble in a variety of organic solvents, such as for example hexane, toluene, xylene, ethyl acetate, acetone, acetonitrile, dichloromethane, methanol, ethanol, and the like, or combinations thereof. In such embodiment, the photochromic dye can be characterized by a solubility of from about 5 mg/ml to about 80 mg/ml, alternatively from about 5 mg/ml to about 20 mg/ml, alternatively from about 20 mg/ml to about 50 mg/ml, or alternatively from about 50 mg/ml to about 80 mg/ml. As will be appreciated by one of skill in the art, and with the help of this disclosure, the solubility of the dye in various solvents (e.g., organic solvent) provides for an easier incorporation of the dye in various manufactured articles.

In an embodiment, a photochromic dye composition comprising a photochromic dye can further comprise a carrier vehicle. Generally, a carrier vehicle refers to an inert material that has the purpose of transporting or carrying an active substance (e.g., a photochromic dye). As will be appreciated by one of skill in the art, and with the help of this disclosure, the carrier vehicle provides for an easier incorporation of the photochromic dye in the polymeric material, as will be disclosed in more detail later herein.

In some embodiments, the carrier vehicle can be a liquid. In such embodiments, the carrier vehicle can comprise an organic solvent of the type disclosed herein.

In other embodiments, the carrier vehicle can be a solid. In such embodiments, the carrier vehicle can comprise a solid substrate, such as for example a temporary support (e.g., a sheet of craft paper, filter paper, aluminum foil, polymer film or fabric, etc.), wherein the temporary support can provide for transferring the photochromic dye to the polymeric material, as will be disclosed in more detail later herein.

In an embodiment, a photochromic dye of the type disclosed herein can be present in a photochromic dye composition in an amount of from about 1 ppm to about 2,000 ppm, alternatively from about 10 ppm to about 1,000 ppm, or alternatively from about 50 ppm to about 500 ppm, based on the weight of the photochromic dye composition.

In an embodiment, the photochromic dye composition can comprise a photochromic dye and a polymeric material, wherein the polymeric material can be transparent. Generally, a transparent or optically transparent material allows light to pass through the material without being scattered. Transparent materials can also be referred to as clear or optically clear materials.

Nonlimiting examples of polymeric materials suitable for use in the present disclosure in photochromic dye compositions include thermoplastic polymers, polyacrylates, poly (alkylacrylates), polymethylmethacrylates (PMMAs), cellulose acetate, cellulose triacetate, cellulose acetate propionate, cellulose acetate butyrate, polyolefins, polypropylene, polyethylene, ethylene/propylene copolymers, propylene/butene copolymers, ethylene/propylene/butylene terpolymers, poly(vinyl acetate), poly(vinyl alcohol), polyurethanes, polycarbonates, bisphenol A and sebacic acid based copolymers, polycarbonate/polyester blends, polyethylene terephthalate (PET), polystyrene, poly(styrene/methylmethacrylate) copolymers, poly(styrene/acrylonitrile) copolymers, polyvinyl butyral, nylon, and the like, copolymers thereof, blends thereof, or combinations thereof.

In an embodiment, the thermoplastic polymers can comprise polymers of one or more monomers selected from the group consisting of polyol(allylcarbonate), alkyl carbonates, multifunctional acrylates, multifunctional methacrylates, cellulose acetates, cellulose triacetates, cellulose acetate propionate, nitrocellulose, cellulose acetate balynete, vinyl alcohol, vinyl chloride, vinylidene chloride, and diacylidene pentaerythritol.

In an embodiment, transparent copolymers and blends of transparent polymers or copolymers of the polymeric materials can also be used in the photochromic dye composition. Polymeric materials suitable for use in the present disclosure in photochromic dye compositions are described in more detail in U.S. Pat. No. 6,114,437, which is incorporated by reference herein in its entirety. For purposes of the disclosure herein, the polymeric material can also be referred to as a "host material." The terms "polymeric material" and "host material" can be used interchangeably for purposes of the disclosure herein.

Generally, the polymeric host material can be transparent, but may be translucent or even opaque. As will be appreciated by one of skill in the art, and with the help of this disclosure, the polymeric material need only be transparent to that portion of the electromagnetic spectrum which activates the photochromic dye, i.e., wavelength of UV radiation that produces the open merocyanine form of the dye and to that portion of the visible spectrum that includes the absorption maximum wavelength of the substance in its UV-activated form, i.e., the open merocyanine form. Further, the polymeric material color should not be such that it masks the color of the activated form of the photochromic dye, so a change in color can be readily apparent to an observer.

In some embodiments, the polymeric material can be a transparent solid or an optically clear material, e.g., a material suitable for optical applications, such as ophthalmic lenses, windows, automotive transparencies, automotive windshields, automotive sunroofs, aircraft transparencies, plastic sheeting, etc.

In an embodiment, the photochromic dye composition can further comprise any suitable additives. Such additives can be used singularly or in combination, and can be added to the photochromic dye composition by using any suitable methodology.

Nonlimiting examples of additives for use in the present disclosure in photochromic dye compositions include UV absorbers, hindered amine light stabilizers, singlet-oxygen quenchers (e.g., 1,4-di azabicyclo[2.2.2]octane or DABCO), excited state deactivators (e.g., organic nickel complexes), and the like, or combinations thereof. Such additives can improve the properties of the photochromic dye composition by increasing durability and light fatigue resistance (e.g., increase dye life).

In an embodiment, the UV absorber comprises a commercially available UV absorber, such as for example TINUVIN 329 light stabilizer, which is 2-(2H-benzotriazol-2-yl)-4-(1,1,3,3-tetramethylbutyl)phenol available from BASF; CYASORB UV1084 light stabilizer, which is [2,2'-thiobis(4-t-octylphenolato)]-n-butylamine nickel II available from Cytec Industries Inc.; and the like; or combinations thereof.

In an embodiment, the hindered amine light stabilizer comprises a commercially available hindered amine light stabilizer, such as for example UVASIL 299 hindered amine stabilizer, which protects organic polymers against degradation caused by exposure to UV radiation, and is available from Great Lakes Chemical Corporation; TINUVIN 770 hindered amine light stabilizer, which is a low molecular weight hindered amine light stabilizer (HALS) for applications demanding particularly high light stability, and is available from BASF; TINUVIN 622 oligomeric hindered amine light stabilizer, which is a light stabilizer for all applications calling for low volatility and minimal migration, and is available from BASF; CHIMASSORB 944 oligomeric hindered amine light stabilizer, which is a high molecular weight hindered amine light stabilizer, and is available from BASF; TINUVIN 144 hindered amine light stabilizer, which is a light stabilizer of the HALS class also containing an antioxidant moiety of the sterically hindered phenol type, and is available from BASF; and the like; or combinations thereof.

In an embodiment, the additives can be present in the photochromic dye composition in an amount from about 0.0001 wt. % to about 5.0 wt. %, alternatively from about 0.001 wt. % to about 3.0 wt. %, alternatively from about 0.01 wt. % to about 2.0 wt. %, or alternatively from about 0.1 wt. % to about 1.0 wt. %, based on total weight of the composition.

In an embodiment, the photochromic dye, and the polymeric material, as well as any optional additives, can be combined (e.g., contacted, blended, mixed etc.) to yield photochromic dye compositions by using any suitable mixing means.

In an embodiment, the photochromic dye of the present disclosure can be dissolved or dispersed in a suitable polymeric material (e.g., host material), such as for example by imbibition.

In an embodiment, the photochromic dye of the present disclosure can be dispersed into the polymeric material by "imbibition." Generally, imbibition refers to diffusion or permeation of the photochromic dye into the polymeric material by a suitable transfer mechanism such as permeation of the photochromic dye alone into the polymeric material, immersion (e.g., immersion of the polymeric material in a photochromic dye solution), solvent assisted transfer absorption of the photochromic dye into a porous polymer, thermal transfer, vapor phase transfer, and the like, or combinations thereof. Suitable methods by which the photochromic dye can be applied to or incorporated into the polymeric material are described in more detail in European Patent Nos. 141407; 0254020; and U.S. Pat. No. 5,066,818; each of which is incorporated by reference herein in its entirety.

In an embodiment, imbibition of the photochromic dye into the polymeric material can be achieved by immersion of the polymeric material in a hot solution of the photochromic dye, or by thermal transfer; by providing the photochromic dye as a separate layer between adjacent layers of the polymeric material (e.g., as a part of a polymer film); by applying the photochromic dye as part of a coating placed on a surface of the polymeric material; and the like; or combinations thereof.

In an embodiment, the photochromic dye can be mixed with a polymerizable composition that, upon curing, can produce a polymeric host material and the polymerizable composition can be cast as a film, sheet or lens, injection molded or otherwise formed into a sheet or lens, or polymerized by emulsion or suspension polymerization to form a photochromic particulate material that can be used as a pigment (e.g., dye).

In another embodiment, the photochromic dye can be dissolved or dispersed in water, alcohol or other solvents or solvent mixtures (e.g., a carrier vehicle) and then imbibed into a solid polymeric material by immersion of the solid polymeric material for from several minutes to several hours, e.g., from about 2-3 minutes to about 2-4 hours, in a bath of such solution or dispersion. The bath is conventionally at an elevated temperature, usually in the range of from about 50° C. to about 120° C.; however, temperatures higher than 120° C. can be used. When the immersion period is over, the polymeric material can be removed from the bath and dried.

In yet another embodiment, the photochromic dye can be applied to a surface of the polymeric material by any suitable methodology, such as printing (e.g., contact printing, jetted printing, etc.), spraying, brushing, spin-coating, dip-coating from a solution or dispersion of the photochromic dye in the presence of a polymeric binder, and the like, or combinations thereof. Thereafter, the photochromic dye can be imbibed into the polymeric material by heating it, such as for example in an oven, for from about 1 minute to several hours, e.g., about 2 to 3 hours, at temperatures in the range of from about 80° C. to about 180° C., or alternatively from about 100° C. to about 150° C.

In still yet another embodiment, the photochromic dye can be deposited onto or absorbed by a temporary support, e.g., a sheet of craft paper, aluminum foil, polymer film or fabric (e.g., carrier vehicle), which can then be placed in near proximity to or in contact with the polymeric material and heated, e.g., in an oven. This procedure and the procedure in the preceding paragraph can be repeated one or more times to imbibe a desired amount of photochromic dye into the polymeric material.

In still yet another embodiment, the photochromic dye can be dissolved or dispersed in a transparent polymeric material which can be applied to a surface of the polymeric material in the form of an adherent film by any suitable technique, such as spraying, brushing, spin-coating, dip-coating, and the like, or combinations thereof.

In still yet another embodiment, the photochromic dye can be incorporated in or applied to a transparent polymeric material by any of the above-mentioned methods, which can then be placed within another polymeric material as a discrete layer intermediate to adjacent layers of the polymeric material(s).

In still yet another embodiment, a substantially homogeneous film of a photochromic dye composition comprising a photochromic dye and a first polymeric material, wherein the photochromic dye is dissolved in the first polymeric material, can be applied to a surface of a second polymeric material to form a film-bearing polymeric material, wherein the first polymeric material and the second polymeric material can be the same or different. The film-bearing polymeric material can be heated to temperatures near to but below the melting temperature of the photochromic dye for a time sufficient to incorporate a desired amount of the photochromic dye into a surface of the second polymeric material. A photochromic-depleted film can then be removed from the surface of the second polymeric material with a suitable solvent.

In still yet another embodiment, imbibition of photochromic dyes into a polymeric material, e.g., an ophthalmic lens, can be performed readily by dissolving the photochromic dye in a suitable solvent, e.g., toluene, and absorbing the resulting solution into a temporary substrate, such as filter paper or any other suitable substrate as previously described herein. A concentration of the photochromic dye in the solvent can vary and will depend on the solubility of the dye in the solvent used. In some embodiments, the photochromic dye can be present in the solvent at a concentration of from about 5 wt. % to about 15 wt. %, e.g., about 10 wt. %. The temporary substrate can be a flexible material that can take the shape of a surface of the polymeric material on which it is placed if such surface is irregular or not flat, such as a curved surface of a lens.

In some embodiments, the temporary substrate containing the solution of photochromic dye can be dried to remove the solvent and the temporary substrate can be placed in contact with a surface of the polymeric material. Optionally, a metal cap having the shape of the polymeric material surface can be placed on top of the temporary substrate to insure uniform contact across an interface of the temporary substrate and the polymeric material surface. For example, when the polymeric material is a lens, the cap and the temporary substrate could be shaped to conform to the shape of the lens, e.g., the convex or concave surface of the lens. A sandwich comprising the metal cap-temporary substrate-polymeric material can be formed and then heated for a time sufficient to imbibe a desired amount of the photochromic dye into a subsurface of the polymeric material. Heating times can range from about 15 minutes to about 180 minutes, or alternatively from about 45 minutes to about 120 minutes at transfer temperatures of from about 125° C. to about 155° C. In such embodiment, the imbibition can be repeated one or more times, e.g., two or three times, to imbibe the desired amount of photochromic dye into a subsurface of the polymeric material, e.g., to a depth beneath the surface of the polymeric material of up to about 50 microns. In the case of semi-finished lenses, the imbibition process can be performed on the front (convex) surface of the lens to allow finishing (grinding) of the back (concave) surface. Further, the edges of the lens may be ground to remove imperfections before thermally transferring photochromic dyes. If desired, the polymeric material can then be tinted with a color compatible dye, e.g., a bluish-green dye, a gray dye, a brown dye, a yellow-brown dye, etc.

In an embodiment, the photochromic dye composition comprising a photochromic dye as disclosed herein (e.g., a compound characterized by Structure I) can comprise a variety of articles, including, but not limited to lenses for sunglasses, ophthalmic lenses, optical filters, automotive windows, automotive windshields, automotive sunroofs, aircraft windows, ship windows, architectural windows, building windows, agricultural windows, greenhouse windows, "stained glass" windows, toy parts, watches, watch straps, novelty items, paints, inks, electronic devices, electronic switches, non-linear optical devices, optical data storage, and the like, or combinations thereof. As will be appreciated by one of skill in the art, and with the help of this disclosure, at least a portion of the article can comprise the photochromic dye. For example, only a top portion of a car windshield can be tinted with the photochromic dye.

In an embodiment, at least a portion of the article comprising the photochromic dye composition can be transparent in the absence of UV radiation.

In an embodiment, at least a portion of the article can become colored (e.g., can absorb visible light) upon irradiation with UV-A radiation owing to an open merocyanine form of the photochromic dye (e.g., compound characterized by Formula I).

In an embodiment, a photochromic dye composition can comprise a photochromic dye and a polymeric material, wherein the photochromic dye can comprise a compound characterized by Structure A:

Structure A

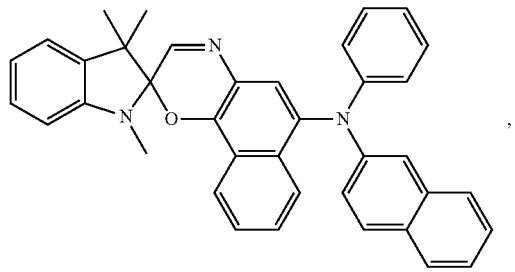

and wherein the polymeric material comprises polycarbonate. In such embodiment, the photochromic dye composition can comprise an ophthalmic lens, wherein the ophthalmic lens can have a bluish-green color upon irradiation with UV-A radiation.

In an embodiment, a photochromic dye composition can comprise a photochromic dye and a polymeric material, wherein the photochromic dye can comprise a compound characterized by Structure A, and wherein the polymeric material comprises any suitable polymeric material as previously disclosed herein.

In an embodiment, the photochromic dye compositions of this disclosure can advantageously display excellent coloring power, e.g., a small amount of dye is necessary for imparting desired photochromic properties to a polymeric material.

In an embodiment, the photochromic dye compositions of this disclosure can advantageously display remarkable fatigue resistance, e.g., increased dye life.

In an embodiment, the photochromic dye compositions of this disclosure can advantageously be synthesized in three steps by using easily accessible reagents. Additional advantages of the photochromic dye compositions of this disclosure can be apparent to one of skill in the art viewing this disclosure.

EXAMPLES

The subject matter having been generally described, the following examples are given as particular embodiments of the disclosure and to demonstrate the practice and advantages thereof. It is understood that the examples are given by way of illustration and are not intended to limit the specification of the claims to follow in any manner.

Example 1

The compound characterized by Structure A was synthesized by reaction of 1,2-naphthoquinone (1a) with N-phenyl-2-naphthyl amine (2a), according to the following reaction scheme:

Nucleophilic addition of N-phenyl-2-naphthyl amine (2a) to 1,2-naphthoquinone (1a) with aqueous ethanol (95% EtOH) at room temperature (RT) followed by air oxidation can produce a compound (3a) in almost quantitative yield. Oxime formation of 1,2-diketone with hydroxyl amine hydrochloride ($H_2N$—OH HCl) can produce the desired mono-oxime derivative (4a) in moderate yield. The final condensation step of the mono-oxime derivative (4a) with 1,3,3-trimethyleneindoline in the presence of triethyl amine ($Et_3N$) under reflux conditions in ethanol can afford the desired spirooxazine compound characterized by Structure A.

Synthesis of Compound (3a):

N-phenyl-2-naphthyl amine (2a) (1.38 g, 6.32 mmol) was added to a solution of 1,2-naphthoquinone (1a) (1 g, 6.32 mmol) in 95% ethanol under air to yield a reaction mixture. The reaction mixture was stirred at room temperature for 2 days and the solvent was evaporated in vacuo to yield a residue. The residue was dissolved in dichloromethane (DCM, 100 ml) and dried over $Na_2SO_4$; and the solvent was evaporated in vacuo to yield a crude product (3a). The obtained crude product (3a) was directly used in the next step without further purification.

Synthesis of Compound (4a):

Hydroxyl amine hydrochloride (296 mg, 4.26 mmol) was added to a solution of compound (3a) (800 mg, 2.13 mmol) in absolute ethanol (30 ml) and the resulting reaction mixture was stirred at room temperature until the complete conversion of starting material (ca. 2h). The solvent was evaporated in vacuo and the resulting residue was dissolved in DCM (100 nil), washed with water, dried over $Na_2SO_4$ and the solvent was evaporated in vacuo to yield a crude

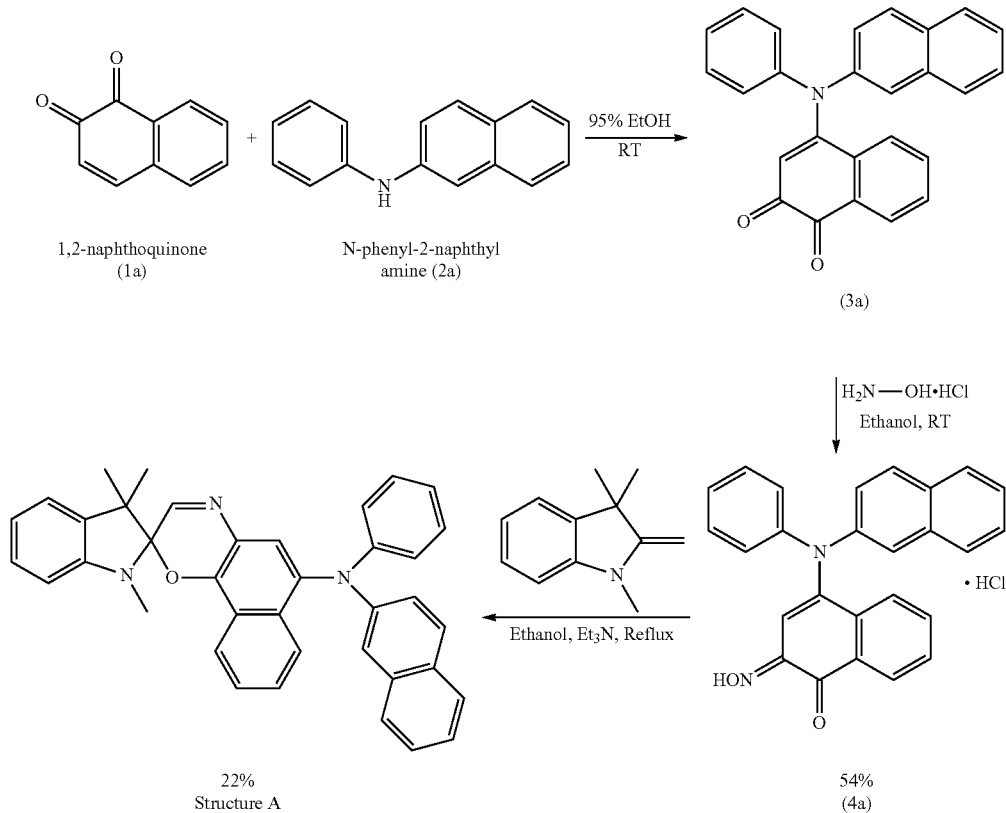

product (4a). The obtained crude product (4a) was purified by column chromatography (hexane/EtOAc: 8/2, Rf: 0.2). The yield for the compound (4a) was 54%. $^1$H-NMR (600 MHz, DMSO): δ=13.38 (hr. s, 1H), 8.12 (d, J=7.0 Hz, 1H), 7.87 (d, J=8.8 Hz, 1H), 7.84 (d, J=7.6 Hz, 1H), 7.72 (d, J=7.6 Hz, 1H), 7.50-7.31 (m, 9H), 7.15-7.09 (m, 2H), 6.77 (s, 1H) $^{13}$C-NMR (600 MHz, CDCl3): δ=181.1, 147.3, 145.7, 144.9, 135.4, 134.4, 134.3 (2C), 133.0, 130.2 (2C), 129.9, 129.7, 129.4, 128.0, 127.8, 127.5, 127.1, 126.5, 125.5, 124.4 (2C), 124.1. 123.9, 119.9, 113.1; LCMS (ESI): m/z: calcd for C26H18N2O2: 391.44 [M+H]+. found: 391.44.

Synthesis of Compound Characterized by Structure A:

Et$_3$N (0.2 ml, 1.52 mmol) and 1,3,3-trimethyl-2-methyleneindoline (131 mg. 0.76 mmol) were added to a stirred solution of compound (4a) (150 mg, 0.38 mmol) in absolute ethanol. The resulting reaction mixture was refluxed until the complete consumption of starting material (ca. 8h). The solvent was evaporated in vacuo and the residue was dissolved in DCM (25 ml), wherein the organic layer was washed with 1N HCl (5 ml), water (5 ml), and brine (5 ml). The resulting crude product (compound characterized by Structure A) was purified by flash chromatography (96% hexane in EtOAc, Rf: 0.25). The yield for the compound characterized by Structure A was 22%. $^1$H-NMR (600 MHz, CDCl3): δ=8.09 (dd, J=8.0, 1.8 Hz, 1H), 7.94 (dd, J=7.0, 1.8 Hz, 1H), 7.74 (d, J=8.2 Hz, 1H), 7.71 (s, 1H), 7.70 (d, J=8.2 Hz, 1H), 7.54 (d, J=8.2 Hz, 1H), 7.50 (s, 1H), 7.37-7.33 (m, 6H), 7.32-7.30 (m, 4H), 7.15 (d, J=7.0 Hz, 1H), 7.13 (d, i=7.0 Hz, 1H), 6.99 (d, J=7.3 Hz, 1H), 6.95 (d, J=6.8 Hz, 1H), 6.63 (d, J=8.3 Hz, 1H), 2.85 (s, 3H), 1.45 (s, 3H), 1.40 (s, 3H). $^{13}$C-NMR (600 MHz, CDCl3): δ=152.5, 148.3, 147.5, 146.1, 140.5, 136.3, 135.8, 134.5, 132.3, 129.5 (3C), 129.2, 128.8, 128.0, 127.6, 127.5, 127.3, 126.8, 126.2, 126.0, 125.3, 124.8, 124.0, 122.6, 122.4, 121.9 (3C), 121.5, 119.8, 117.2, 107.1, 99.4, 51.9, 29.7, 25.5, 21.0; LCMS (ESI): m/z: calcd for C$_{38}$H$_{31}$N$_3$O: 545.93 [M+H]+. found: 545.93.

Example 2

The properties of the compound characterized by Structure A were investigated. More specifically, the absorption spectrum in toluene for the compound characterized by Structure A was recorded, and the data are displayed in FIG. 1. Upon irradiation with UV-A radiation, the compound characterized by Structure A displayed a maximum absorption at 658 nm, and it displayed a bluish-green color.

For the purpose of any U.S. national stage filing from this application, all publications and patents mentioned in this disclosure are incorporated herein by reference in their entireties, for the purpose of describing and disclosing the constructs and methodologies described in those publications, which might be used in connection with the methods of this disclosure. Any publications and patents discussed herein are provided solely for their disclosure prior to the filing date of the present application. Nothing herein is to be construed as an admission that the inventors are not entitled to antedate such disclosure by virtue of prior invention.

In any application before the United States Patent and Trademark Office, the Abstract of this application is provided for the purpose of satisfying the requirements of 37 C.F.R. §1.72 and the purpose stated in 37 C.F.R. §1.72(b) "to enable the United States Patent and Trademark Office and the public generally to determine quickly from a cursory inspection the nature and gist of the technical disclosure." Therefore, the Abstract of this application is not intended to be used to construe the scope of the claims or to limit the scope of the subject matter that is disclosed herein. Moreover, any headings that can be employed herein are also not intended to be used to construe the scope of the claims or to limit the scope of the subject matter that is disclosed herein. Any use of the past tense to describe an example otherwise indicated as constructive or prophetic is not intended to reflect that the constructive or prophetic example has actually been carried out.

The present disclosure is further illustrated by the following examples, which are not to be construed in any way as imposing limitations upon the scope thereof. On the contrary, it is to be clearly understood that resort can be had to various other aspects, embodiments, modifications, and equivalents thereof which, after reading the description herein, can be suggest to one of ordinary skill in the art without departing from the spirit of the present invention or the scope of the appended claims.

Additional Disclosure

The following are enumerated embodiments which are provided as non-limiting examples:

A first embodiment, which is a compound characterized by Formula I:

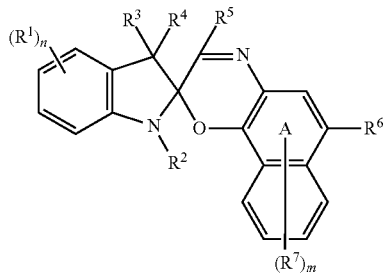

Formula I wherein $R^1$ and $R^7$ can each independently be (i) hydrogen or a group represented by formula —R, —OR, —SR, —COR, or —COOR, wherein R can be hydrogen, an alkyl group, an aryl group, or a heteroaryl group, (ii) a group represented by formula —Z, —CH$_2$Z, —CHZ$_2$, or —CZ$_3$, wherein Z can be a halogen, or (iii) —NO$_2$, —CN, or —SCN; wherein n is an integer from 1 to 4; wherein m is an integer from 1 to 5; wherein $R^2$ can be hydrogen, an alkyl group, a $C_1$ to $C_{20}$ alkyl group, an alkenyl group, a phenyl group, a mono-substituted phenyl group, a di-substituted phenyl group, a tri-substituted phenyl group, a phenylalkyl group, a benzyl group, a carbocyclic group, an alkylcarbocyclic group, a heterocyclic group, a heterocycloalkyl group, or an alkoxy group; wherein $R^3$ and $R^4$ can each independently be hydrogen, an alkyl group, an alkenyl group, a phenyl group, a mono-substituted phenyl group, a di-substituted phenyl group, a tri-substituted phenyl group, a phenylalkyl group, or a benzyl group, or wherein $R^3$ and $R^4$ are both part of the same alicyclic ring, wherein the alicyclic ring comprises a spirocarbon, wherein $R^3$ and $R^4$ are both linked to the spirocarbon, and wherein the alicyclic ring can be a cycloalkyl, norbornane, or adamantane; wherein $R^5$ can be hydrogen, an alkyl group, an alkoxy group, an aryl group, a heteroaryl group, or an amino group; and wherein $R^6$ can be an amino group represented by formula —NR'R", or an amino group comprising a heterocycloalkyl ring or a substituted heterocycloalkyl ring, wherein R' and R" can each independently be hydrogen, an alkyl group, a cycloalkyl group, an aryl group, a phenyl group, a mono-substituted phenyl group, a di-substituted phenyl group, a tri-substituted phenyl group, a naphthyl group, or a substituted naphthyl group.

A second embodiment, which is the compound of the first embodiment, wherein $R^1$ and $R^7$ can each independently be selected from the group consisting of hydrogen, a methyl group, an ethyl group, a n-propyl group, an iso-propyl group, a n-butyl group, an iso-butyl group, a sec-butyl group, and a tert-butyl group.

A third embodiment, which is the compound of the second embodiment, wherein $R^1$ is hydrogen.

A fourth embodiment, which is the compound of any of the second through the third embodiments, wherein $R^7$ is hydrogen.

A fifth embodiment, which is the compound of any of the first through the fourth embodiments, wherein $R^2$ is selected from the group consisting of a methyl group, an ethyl group, a n-propyl group, an iso-propyl group, a n-butyl group, an iso-butyl group, a sec-butyl group, and a tert-butyl group.

A sixth embodiment, which is the compound of any of the first through the fifth embodiments, wherein $R^3$ and $R^4$ can each independently be selected from the group consisting of a methyl group, an ethyl group, a n-propyl group, an iso-propyl group, a n-butyl group, an iso-butyl group, a sec-butyl group, and a tert-butyl group.

A seventh embodiment, which is the compound of any of the first through the sixth embodiments, wherein $R^5$ is hydrogen.

An eighth embodiment, which is the compound of any of the first through the seventh embodiments, wherein $R^6$ is an amino group represented by formula —NR'R".

A ninth embodiment, which is the compound of the eighth embodiment, wherein R' and R" can each independently be a $C_6$ to $C_{10}$ aryl group.

A tenth embodiment, which is the compound of any of the eighth through the ninth embodiments, wherein R' and R" can each independently be selected from the group consisting of phenyl, 1-naphthyl, and 2-naphthyl.

An eleventh embodiment, which is the compound of any of the first through the tenth embodiments, wherein $R^6$ is a N-phenyl-2-naphthyl amino group.

A twelfth embodiment, which is the compound of any of the first through the eleventh embodiments, wherein the compound characterized by Formula I has Structure A:

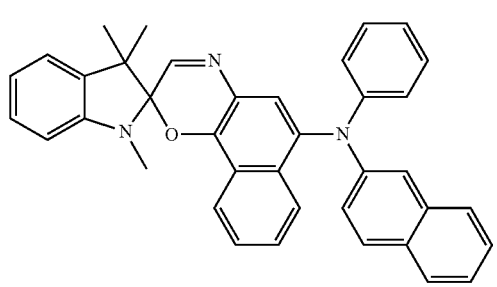

Structure A

A thirteenth embodiment, which is the compound of any of the first through the twelfth embodiments, wherein the compound characterized by Formula I is a photochromic dye.

A fourteenth embodiment, which is the compound of any of the first through the thirteenth embodiments, wherein the compound characterized by Formula I exhibits a bathochromic shift upon irradiation with UV-A radiation.

A fifteenth embodiment, which is the compound of any of the first through the fourteenth embodiments, wherein the compound characterized by Formula I forms an open merocyanine form of the compound characterized by Formula I upon irradiation with UV-A radiation.

A sixteenth embodiment, which is the compound of the fifteenth embodiment, wherein the open merocyanine form the compound characterized by Formula I absorbs visible light having a wavelength of from about 400 nm to about 750 nm.

A seventeenth embodiment, which is the compound of the twelfth embodiment, wherein the compound having Structure A forms an open merocyanine form having Structure A1 upon irradiation with UV-A radiation:

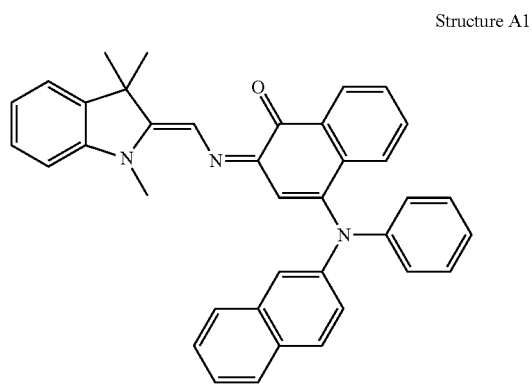 [SMILES: CN1/C(=C\N=C2\C=C(N(c3ccccc3)c3ccc4ccccc4c3)c3ccccc3C2=O)C(C)(C)c2ccccc21]

Structure A1

An eighteenth embodiment, which is the compound of the seventeenth embodiment, wherein the open merocyanine form having Structure A1 absorbs visible light having a wavelength of from about 540 nm to about 750 nm.

A nineteenth embodiment, which is the compound of the first through the eighteenth embodiments, wherein the compound characterized by Formula I is characterized by a solubility of from about 5 mg/ml to about 80 mg/ml.

A twentieth embodiment, which is a photochromic dye composition comprising the compound of any of the first through the nineteenth embodiments and a carrier vehicle.

A twenty-first embodiment, which is the composition of the twentieth embodiment wherein the carrier vehicle is an organic solvent.

A twenty-second embodiment, which is the composition of the twenty-first embodiment wherein the organic solvent comprises hexane, toluene, xylene, ethyl acetate, acetone, acetonitrile, dichloromethane, methanol, ethanol, or combinations thereof.

A twenty-third embodiment, which is a photochromic dye composition comprising a photochromic dye and a polymeric material, wherein the photochromic dye can comprise at least one compound represented by Formula I:

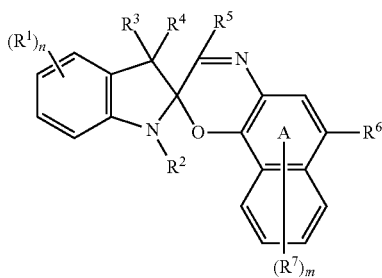

Formula I wherein $R^1$ and $R^7$ can each independently be (i) hydrogen or a group represented by formula —R, —OR, —SR, —COR, or —COOR, wherein R can be hydrogen, an alkyl group, an aryl group, or a heteroaryl group, (ii) a group represented by formula —Z, —CH$_2$Z, —CHZ$_2$, or —CZ$_3$, wherein Z can be a halogen, or (iii) —NO$_2$, —CN, or —SCN; wherein n is an integer from 1 to 4; wherein m is an integer from 1 to 5; wherein $R^2$ can be hydrogen, an alkyl group, a $C_1$ to $C_{20}$ alkyl group, an alkenyl group, a phenyl group, a mono-substituted phenyl group, a di-substituted phenyl group, a tri-substituted phenyl group, a phenylalkyl group, a benzyl group, a carbocyclic group, an alkylcarbocyclic group, a heterocyclic group, a heterocycloalkyl group, or an alkoxy group; wherein $R^3$ and $R^4$ can each independently be hydrogen, an alkyl group, an alkenyl group, a phenyl group, a mono-substituted phenyl group, a di-substituted phenyl group, a tri-substituted phenyl group, a phenylalkyl group, or a benzyl group, or wherein $R^3$ and $R^4$ are both part of the same alicyclic ring, wherein the alicyclic ring comprises a spirocarbon, wherein $R^3$ and $R^4$ are both linked to the spirocarbon, and wherein the alicyclic ring can be a cycloalkyl, norbornane, or adamantane; wherein $R^5$ can be hydrogen, an alkyl group, an alkoxy group, an aryl group, a heteroaryl group, or an amino group; and wherein $R^6$ can be an amino group represented by formula —NR'R", or an amino group comprising a heterocycloalkyl ring or a substituted heterocycloalkyl ring, wherein R' and R" can each independently be hydrogen, an alkyl group, a cycloalkyl group, an aryl group, a phenyl group, a mono-substituted phenyl group, a di-substituted phenyl group, a tri-substituted phenyl group, a naphthyl group, or a substituted naphthyl group.

A twenty-fourth embodiment, which is the photochromic dye composition of the twenty-third embodiment, wherein the polymeric material comprises thermoplastic polymers, polyacrylates, poly(alkylacrylates), polymethylmethacrylates, cellulose acetate, cellulose triacetate, cellulose acetate propionate, cellulose acetate butyrate, polyolefins, polypropylene, polyethylene, ethylene/propylene copolymers, propylene/butene copolymers, ethylene/propylene/butylene terpolymers, poly(vinyl acetate), poly(vinyl alcohol), polyurethanes, polycarbonates, bisphenol A and sebacic acid based copolymers, polycarbonate/polyester blends, polyethylene terephthalate, polystyrene, poly(styrene/methylmethacrylate) copolymers, poly(styrene/acrylonitrile) copolymers, polyvinyl butyral, nylon, copolymers thereof, blends thereof, or combinations thereof.

A twenty-fifth embodiment, which is the photochromic dye composition of the twenty-fourth embodiment, wherein the thermoplastic polymers comprise polymers of one or more monomers selected from the group consisting of polyol(allylcarbonate), alkyl carbonates, multifunctional acrylates, multifunctional methacrylates, cellulose acetates, cellulose triacetates, cellulose acetate propionate, nitrocellulose, cellulose acetate balynete, vinyl alcohol, vinyl chloride, vinylidene chloride, and diacylidene pentaerythritol.

A twenty-sixth embodiment, which is the photochromic dye composition of any of the twenty-third through the twenty-fifth embodiments, wherein the polymeric material is transparent.

A twenty-seventh embodiment, which is the photochromic dye composition of any of the twenty-third through the twenty-sixth embodiments, further comprising UV absorbers, hindered amine light stabilizers, singlet-oxygen quenchers, 1,4-diazabicyclo[2.2.2]octane, excited state deactivators, organic nickel complexes, or combinations thereof.

A twenty-eighth embodiment, which is an article comprising the photochromic dye composition of any of the twenty-third through the twenty-seventh embodiments.

A twenty-ninth embodiment, which is the article of the twenty-eighth embodiment comprising lenses for sunglasses, ophthalmic lenses, optical filters, automotive windows, automotive windshields, automotive sunroofs, aircraft windows, ship windows, architectural windows, building windows, agricultural windows, greenhouse windows, stained glass windows, toy parts, watches, watch straps, novelty items, paints, inks, electronic devices, electronic switches, non-linear optical devices, optical data storage, or combinations thereof.

A thirtieth embodiment, which is the article of any of the twenty-eighth through the twenty-ninth embodiments, wherein at least a portion of the article is transparent in the absence of UV radiation.

A thirty-first embodiment, which is the article of any of the twenty-eighth through the thirtieth embodiments, wherein at least a portion of the article exhibits a bathochromic shift upon irradiation with UV-A radiation.

A thirty-second embodiment, which is the article of the twenty-eighth through the thirty-first embodiments, wherein at least a portion of the article becomes colored upon irradiation with UV-A radiation owing to an open merocyanine form of the compound characterized by Formula I.

A thirty-third embodiment, which is a photochromic dye comprising at least one compound characterized by Formula I:

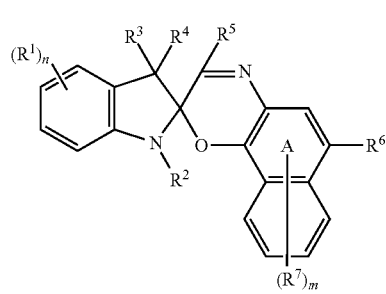

Formula I wherein $R^1$ and $R^7$ can each independently be (i) hydrogen or a group represented by formula —R, —OR, —SR, —COR, or —COOR, wherein R can be hydrogen, an alkyl group, an aryl group, or a heteroaryl group, (ii) a group represented by formula —Z, —CH$_2$Z, —CHZ$_2$, or —CZ$_3$, wherein Z can be a halogen, or (iii) —NO$_2$, —CN, or —SCN; wherein n is an integer from 1 to 4; wherein m is an integer from 1 to 5; wherein $R^2$ can be hydrogen, an alkyl group, a $C_1$ to $C_{20}$ alkyl group, an alkenyl group, a phenyl group, a mono-substituted phenyl group, a di-substituted phenyl group, a tri-substituted phenyl group, a phenylalkyl group, a benzyl group, a carbocyclic group, an alkylcarbocyclic group, a heterocyclic group, a heterocycloalkyl group, or an alkoxy group; wherein $R^3$ and $R^4$ can each independently be hydrogen, an alkyl group, an alkenyl group, a phenyl group, a mono-substituted phenyl group, a di-substituted phenyl group, a tri-substituted phenyl group, a phenylalkyl group, or a benzyl group, or wherein $R^3$ and $R^4$ are both part of the same alicyclic ring, wherein the alicyclic ring comprises a spirocarbon, wherein $R^3$ and $R^4$ are both linked to the spirocarbon, and wherein the alicyclic ring can be a cycloalkyl, norbornane, or adamantane; wherein $R^5$ can be hydrogen, an alkyl group, an alkoxy group, an aryl group, a heteroaryl group, or an amino group; and wherein $R^6$ can be an amino group represented by formula —NR'R", or an amino group comprising a heterocycloalkyl ring or a substituted heterocycloalkyl ring, wherein R' and R" can each independently be hydrogen, an alkyl group, a cycloalkyl group, an aryl group, a phenyl group, a mono-substituted phenyl group, a di-substituted phenyl group, a tri-substituted phenyl group, a naphthyl group, or a substituted naphthyl group.

While embodiments of the disclosure have been shown and described, modifications thereof can be made without departing from the spirit and teachings of the invention. The embodiments and examples described herein are exemplary only, and are not intended to be limiting. Many variations and modifications of the invention disclosed herein are possible and are within the scope of the invention.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention. The disclosures of all patents, patent applications, and publications cited herein are hereby incorporated by reference.

What is claimed is:

1. A compound characterized by Formula I:

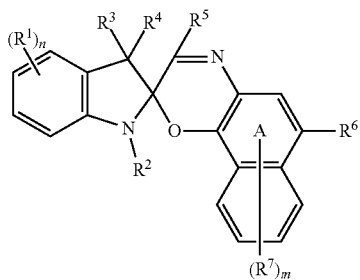

Formula I wherein $R^1$ and $R^7$ can each independently be (i) hydrogen or a group represented by formula —R, —OR, —SR, —COR, or —COOR, wherein R can be hydrogen, an alkyl group, an aryl group, or a heteroaryl group, (ii) a group represented by formula —Z, —CH$_2$Z, —CHZ$_2$, or —CZ$_3$, wherein Z can be a halogen, or (iii) —NO$_2$, —CN, or —SCN; wherein n is an integer from 1 to 4; wherein m is an integer from 1 to 5; wherein $R^2$ can be hydrogen, an alkyl group, a $C_1$ to $C_{20}$ alkyl group, an alkenyl group, a phenyl group, a mono-substituted phenyl group, a di-substituted phenyl group, a tri-substituted phenyl group, a phenylalkyl group, a benzyl group, a carbocyclic group, an alkylcarbocyclic group, a heterocyclic group, a heterocycloalkyl group, or an alkoxy group; wherein $R^3$ and $R^4$ can each independently be hydrogen, an alkyl group, an alkenyl group, a phenyl group, a mono-substituted phenyl group, a di-substituted phenyl group, a tri-substituted phenyl group, a phenylalkyl group, or a benzyl group, or wherein $R^3$ and $R^4$ are both part of the same alicyclic ring, wherein the alicyclic ring comprises a spirocarbon, wherein $R^3$ and $R^4$ are both linked to the spirocarbon, and wherein the alicyclic ring can be a cycloalkyl, norbornane, or adamantane; wherein $R^5$ can be hydrogen, an alkyl group, an alkoxy group, an aryl group, a heteroaryl group, or an amino group; and wherein $R^6$ can be an amino group represented by formula —NR'R", wherein R' and R" can each independently be a phenyl group, a mono-substituted phenyl group, a di-substituted phenyl group, a tri-substituted phenyl group, a naphthyl group, or a substituted naphthyl group; and wherein the compound characterized by Formula I forms an open merocyanine form of the compound characterized by Formula I upon irradiation with UV-A radiation.

2. The compound of claim 1, wherein $R^1$ and $R^7$ can each independently be selected from the group consisting of hydrogen, a methyl group, an ethyl group, a n-propyl group, an iso-propyl group, a n-butyl group, an iso-butyl group, a sec-butyl group, and a tert-butyl group.

3. The compound of claim 2, wherein $R^1$ is hydrogen.

4. The compound of claim 2, wherein $R^7$ is hydrogen.

5. The compound of claim 1, wherein $R^2$ is selected from the group consisting of a methyl group, an ethyl group, a n-propyl group, an iso-propyl group, a n-butyl group, an iso-butyl group, a sec-butyl group, and a tert-butyl group.

6. The compound of claim 1, wherein $R^3$ and $R^4$ can each independently be selected from the group consisting of a methyl group, an ethyl group, a n-propyl group, an iso-propyl group, a n-butyl group, an iso-butyl group, a sec-butyl group, and a tert-butyl group.

7. The compound of claim 1, wherein $R^5$ is hydrogen.

8. The compound of claim 1, wherein R' and R" can each independently be selected from the group consisting of phenyl, 1-naphthyl, and 2-naphthyl.

9. The compound of claim 1, wherein $R^6$ is a N-phenyl-2-naphthyl amino group.

10. The compound of claim 1, wherein the compound characterized by Formula I has Structure A:

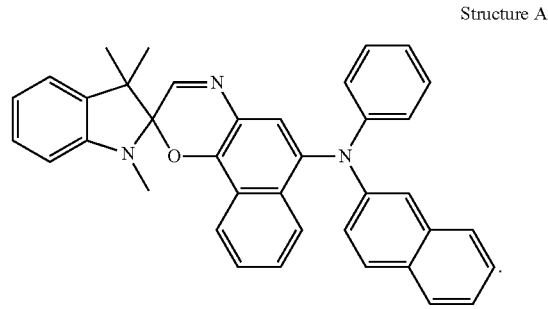 [SMILES: CN1c2ccccc2C(C)(C)C12C=Nc1cc(N(c3ccccc3)c3ccc4ccccc4c3)c3ccccc3c1O2]

Structure A

11. The compound of claim 10, wherein the compound having Structure A forms an open merocyanine form having Structure A1 upon irradiation with UV-A radiation:

Structure A1

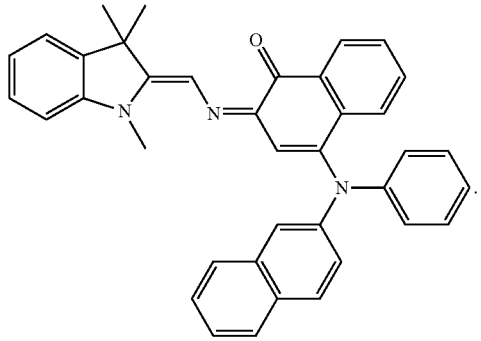

12. The compound of claim 11, wherein the open merocyanine form having Structure A1 absorbs visible light having a wavelength of from about 540 nm to about 750 nm.

13. The compound of claim 1, wherein the compound characterized by Formula I is a photochromic dye.

14. The compound of claim 1, wherein the compound characterized by Formula I exhibits a bathochromic shift upon irradiation with UV-A radiation.

15. The compound of claim 1, wherein the open merocyanine form the compound characterized by Formula I absorbs visible light having a wavelength of from about 400 nm to about 750 nm.

16. The compound of claim 1, wherein the compound characterized by Formula I is characterized by a solubility of from 5 mg/ml to 80 mg/ml or about 5 m/ml to about 80 mg/ml.

17. A photochromic dye composition comprising a photochromic dye and a polymeric material, wherein the photochromic dye can comprise at least one compound represented by Formula I:

Formula I

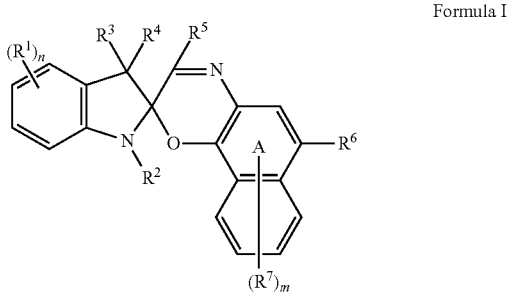

wherein $R^1$ and $R^7$ can each independently be (i) hydrogen or a group represented by formula —R, —OR, —SR, —COR, or —COOR, wherein R can be hydrogen, an alkyl group, an aryl group, or a heteroaryl group, (ii) a group represented by formula —Z, —$CH_2Z$, —$CHZ_2$, or —$CZ_3$, wherein Z can be a halogen, or (iii) —$NO_2$, —CN, or —SCN; wherein n is an integer from 1 to 4; wherein m is an integer from 1 to 5; wherein $R^2$ can be hydrogen, an alkyl group, a $C_1$ to $C_{20}$ alkyl group, an alkenyl group, a phenyl group, a mono-substituted phenyl group, a di-substituted phenyl group, a tri-substituted phenyl group, a phenylalkyl group, a benzyl group, a carbocyclic group, an alkylcarbocyclic group, a heterocyclic group, a heterocycloalkyl group, or an alkoxy group; wherein $R^3$ and $R^4$ can each independently be hydrogen, an alkyl group, an alkenyl group, a phenyl group, a mono-substituted phenyl group, a di-substituted phenyl group, a tri-substituted phenyl group, a phenylalkyl group, or a benzyl group, or wherein $R^3$ and $R^4$ are both part of the same alicyclic ring, wherein the alicyclic ring comprises a spirocarbon, wherein $R^3$ and $R^4$ are both linked to the spirocarbon, and wherein the alicyclic ring can be a cycloalkyl, norbornane, or adamantane; wherein $R^5$ can be hydrogen, an alkyl group, an alkoxy group, an aryl group, a heteroaryl group, or an amino group; and wherein $R^6$ can be an amino group represented by formula —NR'R", wherein R' and R" can each independently be a phenyl group, a mono-substituted phenyl group, a di-substituted phenyl group, a tri-substituted phenyl group, a naphthyl group, or a substituted naphthyl group;

wherein the compound characterized by Formula I forms an open merocyanine form of the compound characterized by Formula I upon irradiation with UV-A radiation; and wherein the polymeric material comprises thermoplastic polymers, polyacrylates, poly(alkylacrylates), polymethylmethacrylates, cellulose acetate, cellulose triacetate, cellulose acetate propionate, cellulose acetate butyrate, polyolefins, polypropylene, polyethylene, ethylene/propylene copolymers, propylene/butene copolymers, ethylene/propylene/butylene terpolymers, poly(vinyl acetate), poly(vinyl alcohol), polyurethanes, polycarbonates, bisphenol A and sebacic acid based copolymers, polycarbonate/polyester blends, polyethylene terephthalate, polystyrene, poly(styrene/methylmethacrylate) copolymers, poly(styrene/acrylonitrile) copolymers, polyvinyl butyral, nylon, copolymers thereof, blends thereof, or combinations thereof.

18. The compound of claim 17, wherein R' and R" can each independently be selected from the group consisting of phenyl, 1-naphthyl, and 2-naphthyl.

19. A compound characterized by Formula I:

Formula I

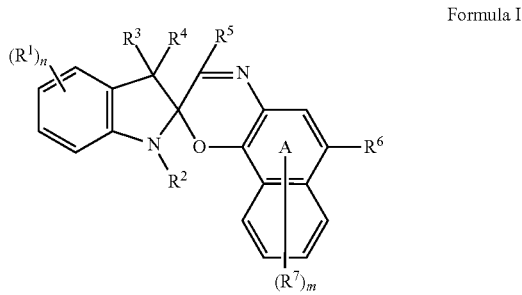

wherein $R^1$ and $R^7$ can each independently be (i) hydrogen or a group represented by formula —R, —OR, —SR, —COR, or —COOR, wherein R can be hydrogen, an alkyl group, an aryl group, or a heteroaryl group, (ii) a group represented by formula —Z, —$CH_2Z$, —$CHZ_2$, or —$CZ_3$, wherein Z can be a halogen, or (iii) —$NO_2$, —CN, or —SCN; wherein n is an integer from 1 to 4; wherein m is an integer from 1 to 5; wherein $R^2$ can be hydrogen, an alkyl group, a $C_1$ to $C_{20}$ alkyl group, an alkenyl group, a phenyl group, a mono-substituted phenyl group, a di-substituted phenyl group, a tri-substituted phenyl group, a phenylalkyl group, a benzyl group, a carbocyclic group, an alkylcarbocyclic group, a heterocyclic group, a heterocycloalkyl group, or an alkoxy group; wherein $R^3$ and $R^4$ can each independently be hydrogen, an alkyl group, an alkenyl group, a phenyl group, a mono-substituted phenyl group, a di-substituted phenyl group, a tri-substituted phenyl group, a phenylalkyl group, or a benzyl group, or wherein $R^3$ and $R^4$ are both part of the same alicyclic ring, wherein the alicyclic ring comprises a spirocarbon, wherein $R^3$ and $R^4$ are both linked to the spirocarbon, and wherein the alicyclic ring can be a cycloalkyl, norbornane, or adamantane; wherein $R^5$ can be hydrogen, an alkyl group, an alkoxy group, an aryl group, a heteroaryl group, or an amino group; and wherein $R^6$ is a N-phenyl-2-naphthyl amino group.

20. A compound characterized by Structure A:

Structure A

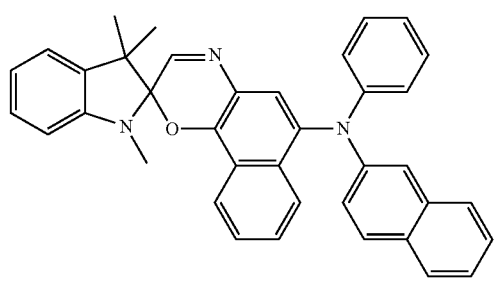

21. The compound of claim 20, wherein the compound having Structure A forms an open merocyanine form having Structure A1 upon irradiation with UV-A radiation:

Structure A1

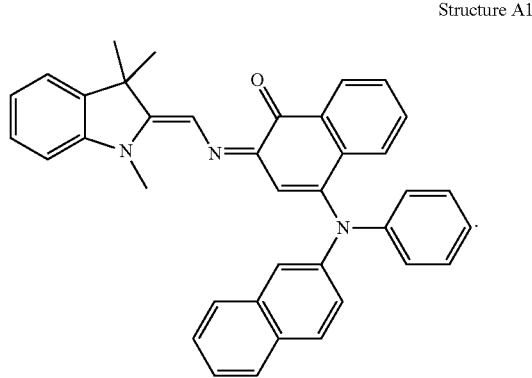 [SMILES: CN1/C(=C\N=C2\C=C(N(c3ccccc3)c3ccc4ccccc4c3)c3ccccc3C2=O)C(C)(C)c2ccccc21]

22. The compound of claim 21, wherein the open merocyanine form having Structure A1 absorbs visible light having a wavelength of from about 540 nm to about 750 nm.

* * * * *

UNITED STATES PATENT AND TRADEMARK OFFICE
CERTIFICATE OF CORRECTION

| | | |
|---|---|---|
| PATENT NO. | : 9,522,921 B2 | |
| APPLICATION NO. | : 15/152710 | |
| DATED | : December 20, 2016 | |
| INVENTOR(S) | : Girish Koripelly et al. | |

It is certified that error appears in the above-identified patent and that said Letters Patent is hereby corrected as shown below:

In the Claims

Claim 16, Column 29, Line 36, replace "about 5m/ml to about" with --about 5mg/ml to about--.

Signed and Sealed this
Fourteenth Day of March, 2017

Michelle K. Lee
*Director of the United States Patent and Trademark Office*